(12) United States Patent
Survant et al.

(10) Patent No.: US 8,768,039 B2
(45) Date of Patent: Jul. 1, 2014

(54) RADIOGRAPHY TEST SYSTEM AND METHOD

(71) Applicant: Florida Power & Light Company, Juno Beach, FL (US)

(72) Inventors: George D. Survant, Gastonia, NC (US); Glenn Martin, Palm Beach Gardens, FL (US); James J. Kovarik, Bartlett, IL (US); Kevin J. Urness, Saint Charles, IL (US); Brent D. Burns, Elgin, IL (US)

(73) Assignee: Florida Power and Light Company, Juno Beach, FL (US)

( * ) Notice: Subject to any disclaimer, the term of this patent is extended or adjusted under 35 U.S.C. 154(b) by 0 days.

(21) Appl. No.: 13/669,625

(22) Filed: Nov. 6, 2012

(65) Prior Publication Data

US 2013/0208858 A1    Aug. 15, 2013

Related U.S. Application Data

(63) Continuation of application No. 13/428,324, filed on Mar. 23, 2012, now abandoned, which is a continuation of application No. 13/208,168, filed on Aug. 11, 2011, now abandoned, which is a continuation of application No. 12/976,076, filed on Dec. 22, 2010, now abandoned, which is a continuation of application No. 11/701,183, filed on Feb. 1, 2007, now Pat. No. 7,912,273.

(51) Int. Cl.
*G06K 9/00* (2006.01)

(52) U.S. Cl.
USPC .......................................................... 382/141

(58) Field of Classification Search
USPC .............................. 382/132, 141–152; 378/98
See application file for complete search history.

(56) References Cited

U.S. PATENT DOCUMENTS

| 3,178,576 A | 4/1965 | Arvanetakis |
| 4,289,030 A | 9/1981 | Alers et al. |
| 4,587,555 A | 5/1986 | Carollo et al. |
| 4,604,649 A | 8/1986 | Carollo et al. |
| 5,192,491 A | 3/1993 | Schulz |
| 5,362,962 A | 11/1994 | Barborak et al. |
| 5,526,691 A | 6/1996 | Latimer et al. |

(Continued)

FOREIGN PATENT DOCUMENTS

| JP | 62008089 | 1/1987 |
| JP | 4048205 | 2/1992 |
| JP | 2001004562 | 1/2001 |

OTHER PUBLICATIONS

Michael Twomey; "Inspection Techniques for Detecting Corrosion Under Insulation;" NDTnet; pp. 1-5; Feb. 1998; vol. 3; No. 2.

*Primary Examiner* — Daniel Mariam
(74) *Attorney, Agent, or Firm* — Feldman Gale, P.A.; Rafael Perez Piñeiro (57) ABSTRACT

A system and method for monitoring degradation of a device having a metal layer and a composite layer, such as a vehicle-mounted boom arm. The system can include a collar mounted on an outer surface of the device, a radiography device movably coupled to the collar, and a monitor. The radiography device can include a source of radiography signals positioned to direct radiography signals through at least a portion of the device and a detector to detect radiography signals that have passed through the device. The monitor can be connected to the detector to display an image of the device generated from the detected radiography signals. Anomalies in the device image can represent degradation in the device.

7 Claims, 8 Drawing Sheets

(56) References Cited

U.S. PATENT DOCUMENTS

| | | |
|---|---|---|
| 5,714,688 A | 2/1998 | Buttram et al. |
| 6,125,703 A | 10/2000 | MacLauchlan et al. |
| 6,157,699 A | 12/2000 | Dunn |
| 6,392,421 B1 | 5/2002 | Amini |
| 6,647,801 B1 | 11/2003 | Deuar |
| 2004/0189289 A1 | 9/2004 | Atherton |

RADIOGRAPHY TEST SYSTEM AND METHOD

CROSS REFERENCE TO RELATED APPLICATIONS

This application is a continuation of U.S. application Ser. No. 13/428,324 filed Mar. 23, 2012 which is a continuation of U.S. application Ser. No. 13/208,168, filed Aug. 11, 2011, which is a continuation of U.S. application Ser. No. 12/976,076, filed Dec. 22, 2010 which is continuation of U.S. application Ser. No. 11/701,183, filed Feb. 1, 2007, the disclosures of which are hereby incorporated herein by reference in their entireties.

FIELD OF THE INVENTION

The invention relates to a system and method for non-destructive examination of degradation, such as corrosion and wear, on a non-visible interior of a device having a metal layer bonded to a composite layer, such as a vehicle-mounted boom arm.

BACKGROUND

Telephone and utility service providers frequently inspect or repair lines, trees, and other objects located at elevated heights. Boom arms fitted with baskets are commonly mounted to vehicles for elevating personnel carried within the basket. Boom arms for such vehicles can be constructed in a variety of configurations, including, for example, an over-center boom arm that can unfold from a horizontal position to a vertical position.

Boom arms are typically hollow tubes that are strong and lightweight with a multi-layer construction. One type of boom arm has an inner metal layer bonded to an intermediate composite layer (e.g., a steel portion that extends 10 to 14 inches across a connection point between fiberglass portions). An outer layer is constructed of a protective material, such as a gel-coat, and is bonded or applied over the composite layer.

The metal layer and the composite layer have different stiffnesses. To provide a smooth transfer of bending stresses created by the load in the basket from the composite layer to the metal layer, the end of the metal layer is tapered over a region around the inner circumference of the boom arm. The tapered region allows a band of stress between the metal layer and the composite layer to dissipate. For example, the tapered region diffuses the stress into a band having a width of about six to ten inches. Without the tapered region, the stress would form a stress line, increasing the likelihood of failure of the composite layer.

The metal layer, and particularly the tapered region of the metal layer, is subject to degradation by, for example, corrosion or wear. When corrosion occurs, rust is produced and the thickness of the metal material at the tapered region is reduced. Because the production of rust does not occur uniformly, the remaining material at the tapered region forms into peaks and valleys, increasing the magnitude of stresses at stress points, rather than across a band. Rust is also worn into the composite layer adjacent to corrosion spots in the metal layer, eroding the composite material and reducing the strength of the composite layer. Finally, as metal and composite material at the tapered region is depleted by degradation, gaps form between the composite layer and the metal layer, reducing the generally uniform transfer of stresses at the tapered region.

Each vehicle-mounted boom arm can be subject to different environmental conditions depending on the use of the boom arm and the local climate. As a result, it is difficult to predict if and when degradation such as corrosion and wear will occur. Furthermore, because degradation occurs on the inside of the boom arm, there may not be any indicators of corrosion, erosion, wear etc. on the exterior or visible surface of the boom arm. In order to access the interior of the boom arm for examination, the boom arm would have to be disassembled or even destroyed with certain boom configurations.

SUMMARY

Accordingly, a need exists for a system and method of examining degradation, such as corrosion and wear, present on a non-visible interior of a device having a metal layer and a composite layer, such as a vehicle-mounted boom arm, without having to destroy or disassemble the device.

In one embodiment, the invention provides a method for non-destructively examining degradation on an interior of a device having a metal layer and a composite layer. Radiography signals are directed through a region of interest of the device, which includes the metal layer and the composite layer. Radiography signals that have passed through the device are detected. An image of the metal layer and the composite layer at the region of interest is generated from the detected radiography signals. Anomalies in the device image representing degradation in the region of interest are identified.

In another embodiment, the invention provides a system for non-destructively examining degradation on an interior of device having a metal layer and a composite layer. The system includes a collar sized and shaped to be mounted on an outer surface of the device, a radiography device movably coupled to the collar, and a monitor. The radiography device includes a source of radiography signals arranged to direct radiography signals through at least a portion of the metal layer and the composite layer and a detector for detecting the radiography signals. The monitor is connected to the detector to display an image of the device generated from the detected radiography signals.

In yet another embodiment, the invention provides a method for monitoring degradation on an interior of a device having a metal layer and a composite layer. A region of interest on an interior of the device is non-destructively examined for degradation, and the degradation is quantified. The device is placed in a first monitoring schedule if substantially no degradation is present on the device. The device is removed from service if a quantity of degradation in excess of a degradation threshold is present on the device. The device is placed in a second monitoring schedule if a quantity of degradation less than the degradation threshold is present on the device.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings, and can include electrical connections or couplings, whether direct or indirect.

Figure 1:
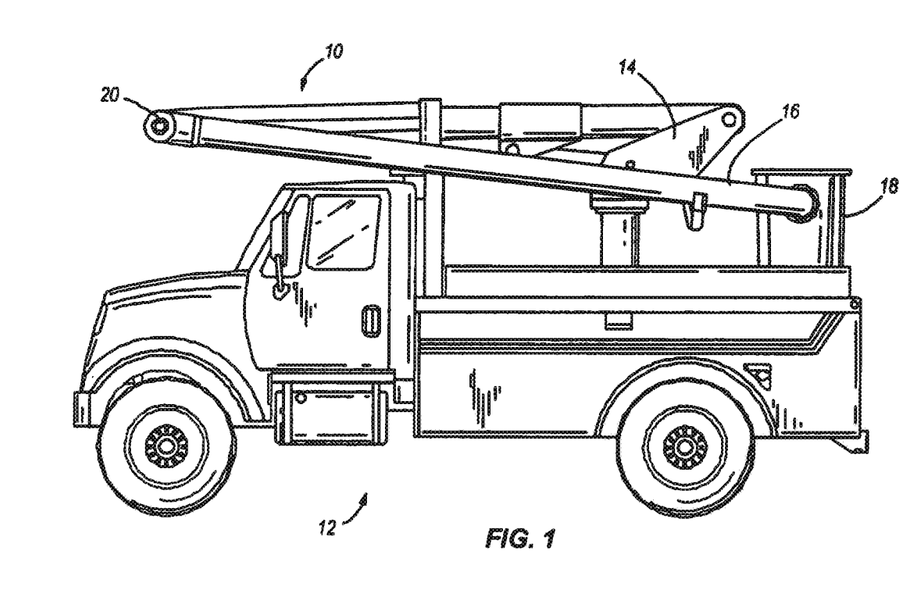
FIG. 1 is a side view of a motorized vehicle with a boom arm in a folded configuration.

FIG. 1 illustrates a boom arm 10 mounted to a motorized vehicle 12 of the type commonly used to access elevated objects, such as power lines and trees. A first end 14 of the boom arm 10 is mounted to the vehicle 12, while a second end 16 of the boom arm 12 is coupled to a passenger basket 18. The boom arm 10 can include an elbow joint 20 so that the boom arm 10 can be stored folded into a horizontal or lengthwise configuration while not in use, as shown in FIG. 1. The boom arm 10 can be unfolded into a vertical position with the basket 18 elevated while in use.

Figure 2:
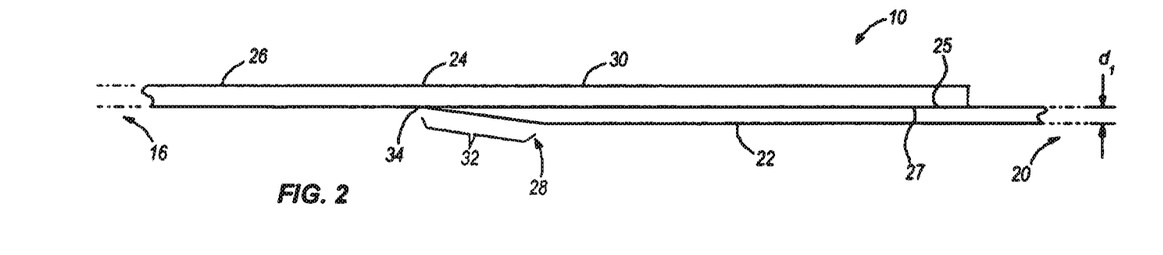
FIG. 2 is a longitudinal cross-sectional view of a portion of a boom arm.
Figure 3:
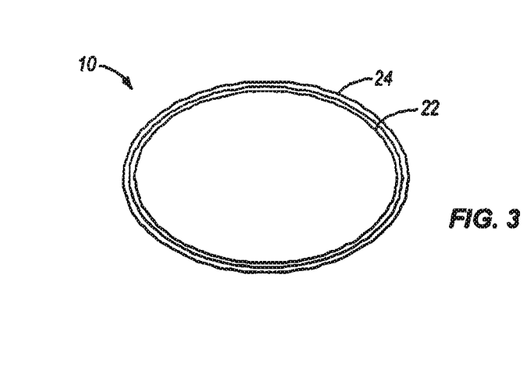
FIG. 3 is a lateral cross-sectional view of the boom arm of FIG. 2.
Figure 5:
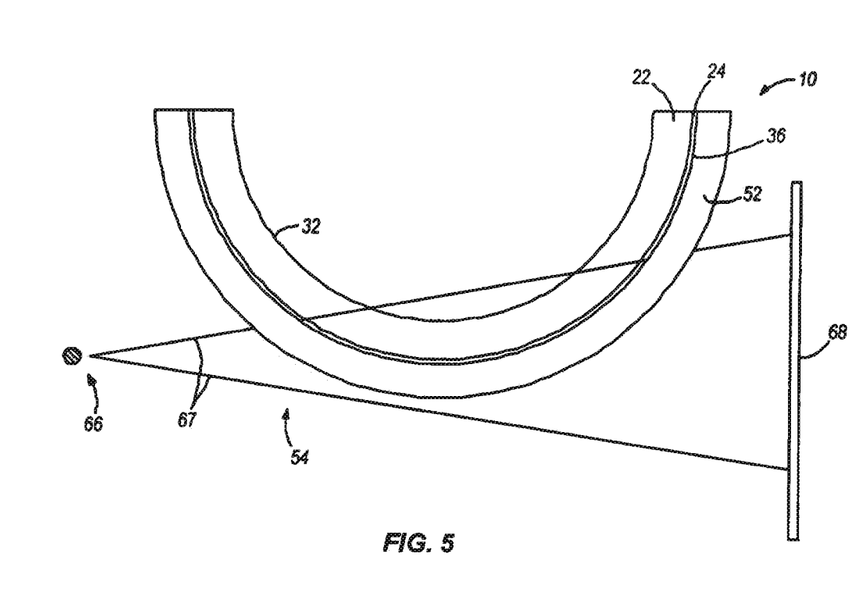
FIG. 5 is a schematic view of a radiography degradation detection system according to one embodiment of the invention operating on a boom arm.

FIGS. 2 and 3 illustrate the construction of the boom arm 10, which is a multi-layer hollow, tubular member. This type of multi-layer construction may also be present in other types of devices or equipment, such as wire spreaders, cranes, platform lifts, cable placers, etc. In the electric utility industry specifically, composite materials are used primarily for construction in order to provide insulation from the electric line voltages. Metals are generally only used to reinforce the joints between composite structures. However, failure occurs at these metal-reinforced joints between composite structures. As shown in FIGS. 2 and 3 for a vehicle-mounted boom arm 10, an inner layer 22 of the boom arm 10 is generally formed of a metal, such as steel. An intermediate layer 24 of the boom arm 10 is generally formed of a composite material, such as fiberglass. An inner surface 25 of the composite layer 24 is bonded to an outer surface 27 of the metal layer 22 to secure the layers to one another. A tapered or transition region 32 is formed at an end 28 of the metal layer 22, where the metal layer 22 is tapered from a first thickness $d_1$ to a pointed or almost pointed edge 34 extending around the circumference of the metal layer 22. However, the transition region 32 may not be tapered in some boom arms. The composite layer 24 is generally longer than the metal layer 22, so that an end 26 of the composite layer 24 forms a tube extending beyond the end 28 of the metal layer 22. As shown in FIG. 5, an outer layer 36, such as a gel coat, of the boom arm 10 can be a protective coating formed or bonded to the intermediate layer 24.

Figure 4:
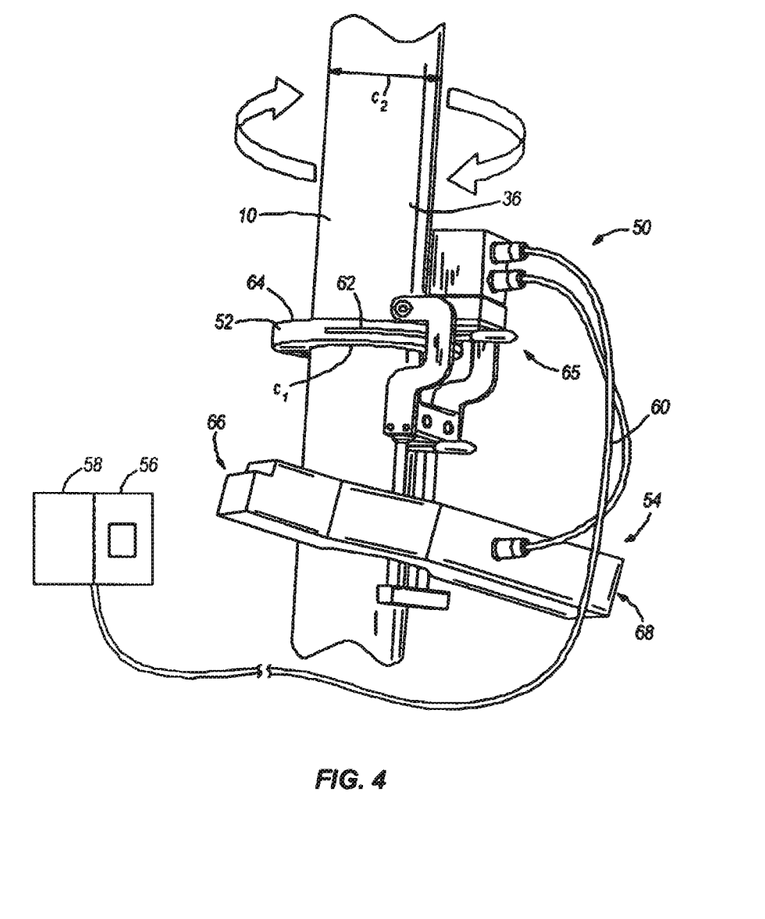
FIG. 4 is a perspective view of a radiography degradation detection system according to one embodiment of the invention mounted to a boom arm.

FIG. 4 illustrates a radiography degradation detection system 50 according to one embodiment of the invention mounted to boom arm 10. The detection system 50 can include a collar 52, a radiography device 54 coupled to the collar 52, and a monitor 56 connected to the radiography device 54.

The collar 52 can be a ring-like member sized and shaped for mounting to an outside of the boom arm 10. An inner circumference $c_1$ of the collar 52 can be slightly greater than an outer circumference $c_2$ of the boom arm 10. The collar 52 can include a hinge or other mechanism to facilitate at least partially opening and mounting the collar 52 to the boom arm 10. The collar 52 can include a securing mechanism 62 to secure the collar 52 to the boom arm 10. The securing mechanism 62 can be a clamp, a compression collar, a magnet, bolts, etc.

In some embodiments, the collar 52 can include a track 64 along which the radiography device 54 can move. The radiography device 54 can be coupled to the collar 52 and can be moved around the circumference of the boom arm 10 by moving along the track 64. The radiography device 54 can include a movement mechanism 65, such as a motor, for coupling the radiography device 54 to the collar 52 and for moving the radiography device 54 along the track 64. In one embodiment, the radiography device 54 can be moved about 360 degrees along the track 64 in order to move around substantially the entire circumference of the boom arm 10. In another embodiment, the radiography device 54 can be moved about 180 degrees along the track 64 or about half of the boom arm circumference.

As shown in FIGS. 4 and 5, the radiography device 54 includes a source 66 of radiography signals 67 and a detector 68 for detecting radiography signals. In one embodiment, the radiography signals 67 are X-ray signals. The source 66 of radiography signals 67 and the detector 68 can be spaced apart on the collar 52 and can be positioned so that radiography signals 67 from the source 66 are directed into the boom arm 10 through both the metal layer 22 and the composite layer 24 toward the detector 68. The detector 68 can be positioned to detect radiography signals 67 which have passed through the boom arm 10. The degradation detection system 50 can be mounted to the boom arm 10 so that the radiography signals 67 pass through a region of interest of the boom arm 10, such as the tapered region 32.

As shown in FIG. 4, the monitor 56 can generate and display an image of the interior of the boom arm 10 from the radiography signals detected by the detector 68. The monitor 56 can be a handheld device, a personal computer, a laptop, or another suitable electronic device and can include a screen for displaying the image and/or data obtained from the detected radiography signals. The detected radiography signals can be displayed as still images or can be displayed as a moving image as the radiography device 54 travels around the boom arm 10 along the track 64. The monitor 56 can display substantially all or a portion of the circumference of the boom arm 10 at a given time. In one embodiment, the monitor 56 displays approximately an 11 degree arc of the boom arm 10 circumference at a given time. The degradation detection system 50 can include a control mechanism 58 that controls movement of the radiography device 54, as well as overall operation of the degradation detection system 50. The degradation detection system 50 can further include cables and connectors 60 for connecting the radiography device 54 to the monitor 56 and/or to other components of the degradation detection system 50. The cables and connectors 60 can be replaced with a wireless connection.

Figure 6:
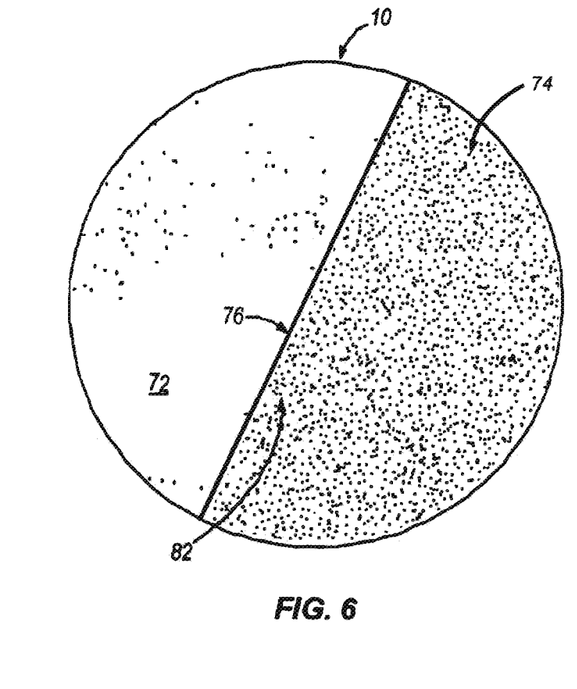
FIG. 6 is an image of a portion of a tapered region of a boom arm with no degradation generated by a radiography degradation detection system according to one embodiment of the invention.

FIG. 6 illustrates an image of the boom arm 10 of FIG. 2 generated by the degradation detection system 50. An area 72 indicates the composite layer 24, and is lighter than an area 74, because composite materials, such as fiberglass, tend to transmit more radiography signals. The area 74 indicates the metal layer 22, and is darker than the area 72, because metal materials, such as steel, tend to block more radiography signals. A demarcation line 76 between the area 72 and the area 74 corresponds to the tapered region 32. As shown in FIG. 6, the demarcation line 76 is a clean, straight line. This mimics the straight edge 34 (as shown in FIG. 2) and the uniform taper of the tapered region 32. In other words, there is little or no degradation in the tapered region 32 of the boom 10. As used herein and in the appended claims, the term "degradation" refers to any type of corrosion, erosion, wear, loss of material, cracking, or any reduction in thickness, height, or width of either the metal layer 22 or the composite layer 24 of the boom arm 10.

Figure 7:
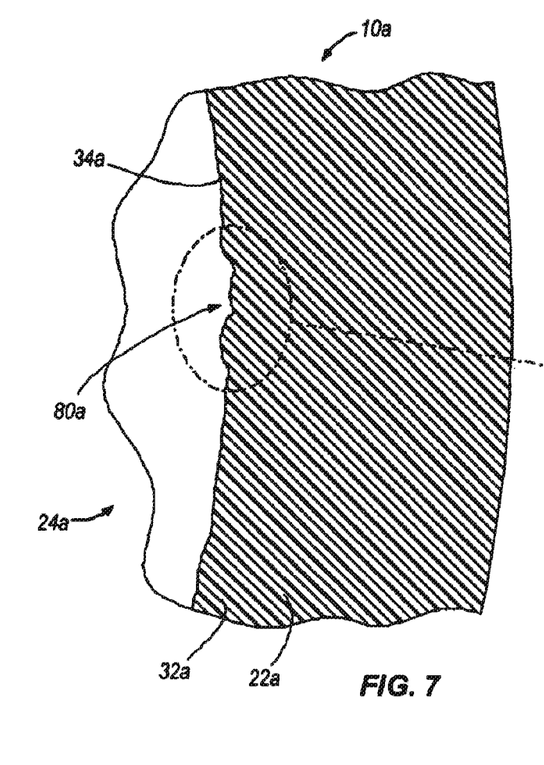
FIG. 7 is an illustration of a portion of a tapered region of an actual boom arm having degradation.
Figure 8:
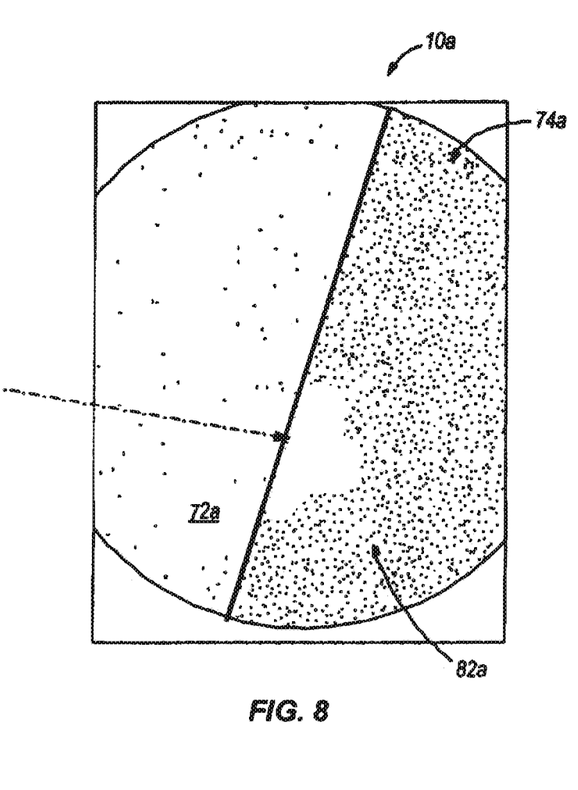
FIG. 8 is an image of the portion of the tapered region of FIG. 7 generated by a radiography degradation detection device according to one embodiment of the invention.

FIG. 7 illustrates a portion of a boom arm 10a in which the transition region 32a has experienced degradation, including corrosion of the metal layer 22 that has formed rust 80a. FIG. 8 illustrates an image of the boom arm 10a of FIG. 7 generated by the degradation detection system 50. The demarcation line 76a from the area 74a (representing the metal layer 22) to the area 72a (representing the composite layer 24) is jagged and fuzzy in comparison to the clean demarcation line 76 in FIG. 6. This is caused by variations in thickness of the composite layer 24 and/or the metal layer 22 due to degradation. In addition, at least a first anomaly 82a is formed in the area 74a representing the metal layer 22, which indicates an area of reduced thickness of the metal layer 22, the composite layer 24, or both. Such lighter shading on the image for an area representing a given material is caused by an increase in detection of radiography signals at the detector 68, which in turn indicates a reduced thickness of the material relative to the surrounding material. This applies to both the metal layer 22 and the composite layer 24. As a result, there is significant degradation in the tapered region 32 of the boom 10a, which could lead to failure of the boom 10a.

Figure 9:
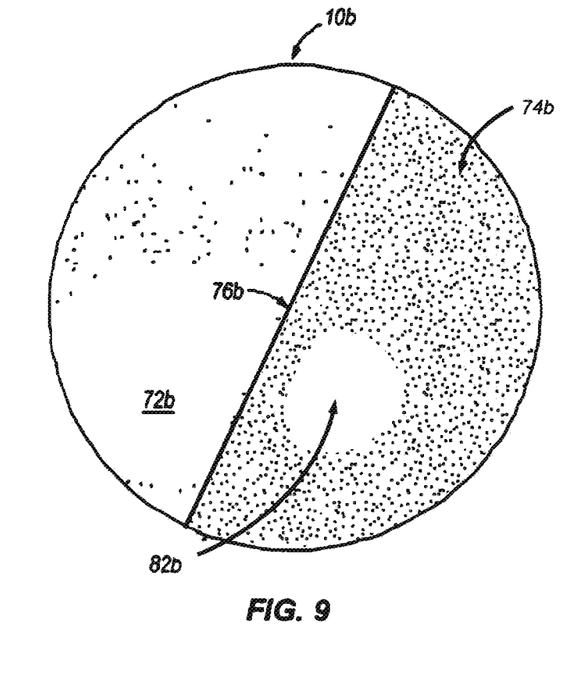
FIG. 9 is an image of a portion of another tapered region having degradation generated by a radiography degradation detection device according to one embodiment of the invention.

FIG. 9 is another image of a portion of a boom arm 10b illustrating an anomaly 82b in area 74b. In contrast to the anomaly 82a shown in FIG. 8, anomaly 82b does not occur at the demarcation line 76b corresponding to edge 34 of the tapered region 32, but is within the tapered region 32. The demarcation line 76b is still relatively clean and straight compared to FIG. 8. However, there is some degradation in the tapered region 32 of the boom 10b.

Jaggedness or fuzziness of the demarcation line 76, spots of lighter shading in either the metal area 74 or the composite area 72, and other phenomena collectively form anomalies in the image of the boom arm 10. Such anomalies mimic the geography of degradation, such as corrosion of the metal layer 22 and erosion of the composite layer 24. Thus, the detected radiography signal image generated by the monitor 56 provides a visual indication of degradation in the interior of the boom arm 10 that closely corresponds to actual degradation present on the boom arm 10.

The degree of degradation, or reduced thickness of one or more of the layers of the boom arm 10, can be indicated by the shading of the anomalies. A substantially lighter anomaly indicates more degradation and more reduced material thickness, while an anomaly that is only slightly lighter indicates less degradation and less reduced material thickness. Thus, the detection system 50 can identify degradation present on the boom arm 10, and in some embodiments, can quantify the degree or amount of degradation by relating shading of anomalies in the image to loss of material thickness. A surface area of degradation can be determined from the area of anomaly locations. The extent of degradation can be categorized and quantified in a number of ways, including, for example, reduction in material thickness, surface area of degradation, surface area of degradation relative to the surface area of the tapered region 32, number of degradation/anomaly locations, etc.

In one embodiment, visual analysis of the image of the boom arm 10 on the monitor 56 is used to identify and/or quantify degradation of the boom arm 10. This analysis can be performed manually by the operator of the degradation detection system 50 upon viewing the image on the monitor 56. In other embodiments, a software program, image analysis tool, or other computerized device can be used to automatically analyze the image of the boom arm 10 to identify and/or quantify degradation. In still other embodiments, a software program, signal analysis tool, or other computerized device can be used to analyze not the image, but the detected radiography signals themselves, in order to identify and/or quantify degradation. Such computerized devices can be installed on a handheld device, laptop, or personal computer that is connected to the monitor 56 and/or the radiography device 54, or can be integrated into the monitor 56. The results of the analysis by the computerized device can be displayed on the monitor 56 or another suitable display device. In addition, such data can be archived, uploaded to a database, transmitted to another party, etc. Finally, in some embodiments, even though identification and quantification of degradation can be carried out automatically by a computerized device, the images of the boom arm 10 can also be displayed on the monitor 56 for visual review by the operator of the degradation detection system 50.

Figure 10:
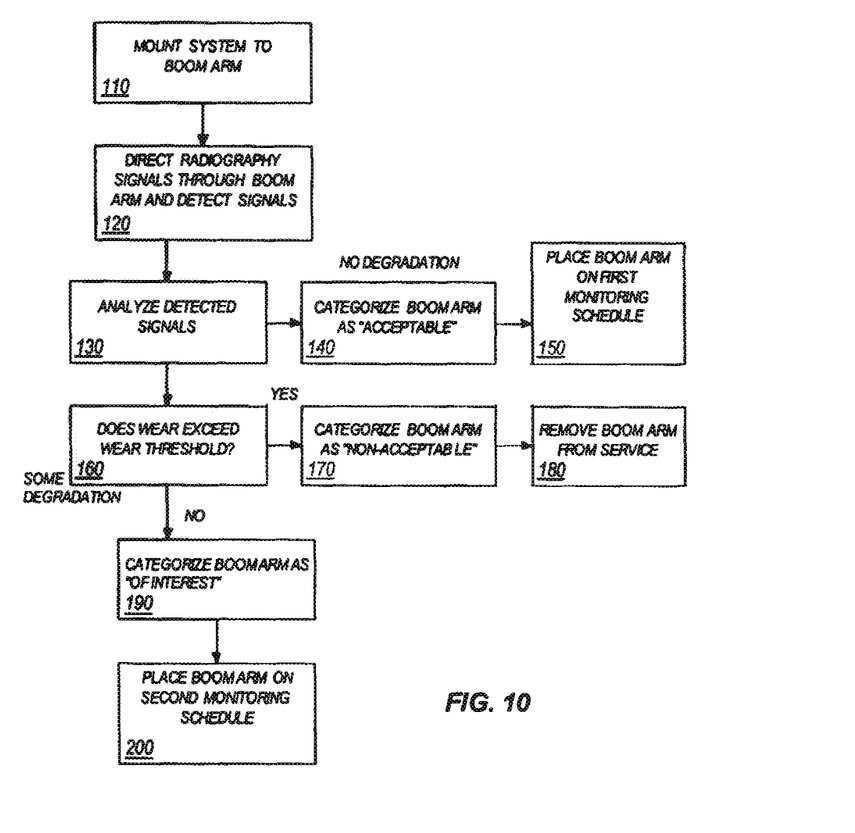
FIG. 10 is a flowchart depicting a method of implementing a boom arm degradation monitoring plan according to one embodiment of the invention.

FIG. 10 is a flowchart illustrating a method for monitoring degradation of a boom arm. The method can be used to monitor the degradation of, for example, a fleet of vehicle-mounted boom arms. The degradation detection system 50 is mounted (at 110) to the boom arm 10 at a region of interest of the boom arm 10, such as the tapered region 32. The degradation detection system 50 is operated to direct (at 120) radiography signals through the region of interest and to detect radiography signals that have passed through the region of interest. The radiography device 54 of the degradation detection system 50 can be rotated around substantially all or a portion of the boom arm 10. The detected radiography signals can be analyzed (at 130) to determine if degradation is present on an interior of the boom arm 10. This analysis can be carried out by visually inspecting an image of the boom arm 10 on the monitor 56, through the use of a computerized device to analyze the detected radiography signals or image, or a combination of both.

Figure 11:
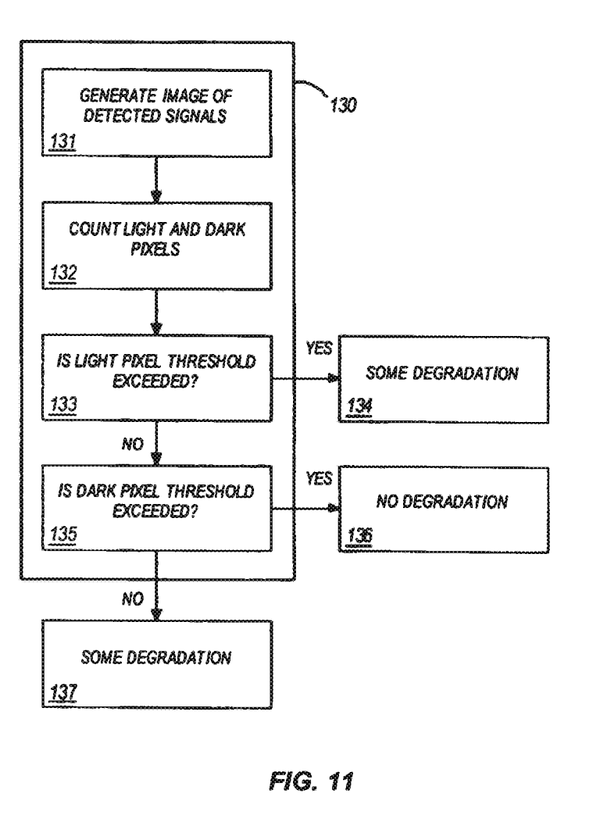
FIG. 11 is a flowchart depicting a method of analyzing detected radiography signals output from a radiography degradation detection device according to one embodiment of the invention.

FIG. 11 is a flowchart illustrating a method of analyzing detected radiography signals (as at 130 in FIG. 10) to determine if degradation is present. In some embodiments, an image of the boom arm 10 is generated from the detected radiography signals (at 131). A computerized device can automatically analyze the image or the radiography signal data to determine how many dark pixels (representing the metal layer 22) versus light pixels (representing the composite layer 24) are present (at 132). The computerized device can compare the number of dark pixels and/or light pixels to how many dark pixels and/or light pixels there should be on a boom arm 10 without any significant or hazardous degradation. The computerized device can also compare the number of dark pixels and/or light pixels to dark and/or light pixel thresholds (at 133 and 135). If the light pixel threshold is exceeded (i.e., there are too many pixels representing composite material or reduced material thickness in the image or data), the computerized device can generate an output indicating that the metal layer 22 has been degraded and that the boom arm 10 should be retired or repaired (at 134). Similarly, if the dark pixel threshold is not exceeded (i.e., there are not enough pixels representing metal material or sufficient material thickness in the image or data), the computerized device can generate an output also indicating that the metal layer 22 has been degraded and that the boom arm 10 should be retired or repaired (at 137). If the light pixel threshold is not exceeded and the dark pixel threshold is exceeded, then the computerized device can generate an output indicating that there is no degradation on the boom arm 10 and the boom arm 10 can be returned to service (at 136). In some embodiments, based on the number of pixels and the comparison to one or more pixel thresholds, the computerized device can generate a definitive output that can be used by personnel to consistently categorize boom arms as being "acceptable", "of interest", or "non-acceptable", as further described below.

Returning to FIG. 10, if no degradation is detected on the boom arm 10, the boom arm 10 is categorized (at 140) as "acceptable". The "acceptable" boom arm 10 can remain in service and can be placed (at 150) into a first or routine monitoring schedule. The first monitoring schedule can, for example, provide for annual degradation tests. If degradation (such as corrosion, wear, or erosion) is detected on the boom arm 10, the extent of the degradation can be compared (at 160) to a degradation threshold. If the detected degradation exceeds the degradation threshold, the boom arm 10 can be categorized as "non-acceptable" (at 170) and can be removed (at 180) from service for retirement or repair. If some degradation is detected, but the extent of the degradation does not exceed the degradation threshold, the boom arm 10 can be categorized (at 190) as "of interest". The "of interest" boom arm 10 can remain in service and can be placed (at 200) into a second or accelerated monitoring schedule. The second monitoring schedule can provide for more frequent, subsequent degradation tests than the first monitoring schedule. The second monitoring schedule can, for example, provide for biannual degradation tests.

The monitoring schedule scheme can vary widely. For example, "of interest" boom arms can be tested every three months on the second monitoring schedule, while "acceptable" boom arms can be tested every six months on the first monitoring schedule. Intermediate degradation thresholds can be used to place the boom arm among multiple "of interest" categories with varying monitoring schedules. The calendar for both routine and accelerated testing schedules can be based in part on the climate in which the boom arm has been or will be located. For example, boom arms located in climates of high humidity and rainfall (such as Florida) can be tested every six months for "acceptable" boom arms and every three months for "of interest" boom arms, while boom arms located in arid climates (such as Arizona) can be tested every year for "acceptable" boom arms and every six months for "of interest" boom arms. In this manner, the testing method of FIGS. 10 and 11 can be applied to a nationwide or global fleet or stock of boom arms.

The degradation threshold can also vary widely. In one embodiment, the degradation threshold is $1/16$ inch. A reduction in height (or a hole inward from the edge of the layer) in the either the metal layer 22 or the composite layer 24 of up to $1/16$ inch can cause the boom arm to be is categorized as "of interest" and a reduction in height (or a hole inward from the edge of the layer) greater than $1/16$ can will cause the boom arm to be categorized as "non-acceptable". In another embodiment, a reduction in thickness of either the metal layer 22 or the composite layer 24 up to 5% of the initial thickness is categorized as "of interest" and a reduction in thickness of greater than 5% is categorized as "non-acceptable". Such degradation thresholds can be dependent upon the initial thickness of the metal layer 22 and the composite layer 24 and/or the material characteristics of the metal layer 22 and the composite layer 24. Furthermore, a first degradation threshold can be applied for reductions in thickness of the metal layer 22 and a second degradation threshold, different from the first degradation threshold, can be applied for reductions in thickness of the composite layer 24. Such degradation threshold limits can also be dependent upon the intended use of the boom arm 10 or a maximum load that can be carried in the basket 18.

The foregoing discussion of degradation threshold assumes that degradation will be quantified in terms of loss of material. In other embodiments, degradation can be quantified in terms of total surface area of degradation, relative surface area of degradation, total number of degradation locations, or other suitable factors. Degradation thresholds for the purposes of boom arm categorization can be selected accordingly. In one embodiment, for example, a boom arm determined to have a total surface area of degradation up to 1 cm$^2$ is categorized as "of interest" and a boom arm having total surface area of degradation greater than 1 cm$^2$ is categorized as "non-acceptable".

Thus, the invention provides, among other things, a system and method for non-destructive examination of degradation on an interior of a boom arm. Various features and advantages of the invention are set forth in the following claims.

The invention claimed is:

1. A method of non-destructively examining degradation on an interior of a device having a metal layer bonded to a composite layer, the method comprising:
   directing radiography signals through a region of interest of the device, the region of interest including the metal layer and the composite layer;
   detecting radiography signals that have passed through the device;
   generating an image of the metal layer and the composite layer at the region of interest from the detected radiography signals; and
   identifying degradation in the region of interest from the image;
      wherein directing radiography signals through the region of interest further comprises rotating a source of radiography signals around at least a portion of an outer circumference of the device.

2. The method of claim 1, further comprising:
displaying the image on a monitor.

3. The method of claim 1, further comprising:
mounting a collar on an outer surface of the device;
movably coupling the collar to a source of said radiography signals directed through said region of interest of the device; and
connecting a monitor to a detector used for detecting said radiography signals that have passed through the device to display an image of the device generated from the detected radiography signals.

4. The method of claim 3, wherein the source of radiography signals is a source of X-ray signals.

5. The method of claim 3 further comprising identifying degradation in the device from the image through use of a computerized device.

6. The method of claim 3 further comprising quantifying degradation in the device from at least one of anomalies in the image and the radiography signals through use of a computerized device.

7. The method of claim 3 further comprising identifying degradation in the image by counting pixels in the image through use of a computerized device.

\* \* \* \* \*